(12) United States Patent
Corey

(10) Patent No.: US 7,183,417 B2
(45) Date of Patent: Feb. 27, 2007

(54) SIMPLE STEREOCONTROLLED SYNTHESIS OF SALINOSPORAMIDE A

(75) Inventor: Elias J. Corey, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 309 days.

(21) Appl. No.: 10/821,621

(22) Filed: Apr. 9, 2004

(65) Prior Publication Data
US 2005/0228186 A1 Oct. 13, 2005

(51) Int. Cl.
C07D 487/02 (2006.01)
(52) U.S. Cl. .................................................. 548/453
(58) Field of Classification Search ................. 548/453
See application file for complete search history.

(56) References Cited

U.S. PATENT DOCUMENTS

| | | | |
|---|---|---|---|
| 5,756,764 A | 5/1998 | Fenteany et al. |
| 5,869,675 A | 2/1999 | Omura et al. |
| 6,133,308 A | 10/2000 | Soucy et al. |
| 6,147,223 A | 11/2000 | Fenteany et al. |
| 6,214,862 B1 | 4/2001 | Fenteany et al. |
| 6,294,560 B1 | 9/2001 | Soucy et al. |
| 6,335,358 B1 | 1/2002 | Fenteany et al. |
| 6,458,825 B1 | 10/2002 | Fenteany et al. |
| 6,566,553 B2 | 5/2003 | Soucy et al. |
| 6,645,999 B1 | 11/2003 | Schreiber et al. |
| 2003/0157695 A1 | 8/2003 | Fenical et al. |

FOREIGN PATENT DOCUMENTS

WO WO 96/32105 10/1996

OTHER PUBLICATIONS

Feeling, R.H.; Buchanan, G.O.; Mincer, T.J.; Kauffman, C.A.; Jensen, P.R.; Fenical, W., Angew. Chem. Int. Ed., Salinosporamide A: A highly Cytotoxic Proteasome Inhibitor from a Novel Microbial Source, a Marine Bacterium of the New Genus Salinospora, 2003, 42, 355-357.
Corey, E.J.; Li, Wei-Dong., Z. Total Synthesis and Biological Activity of Lactacystin, Omuralide and Analogs, Chem. Pharm. Bull., 1999, 47, 1-10.
Corey, E.J., Reichard, G.A.; Kania, R., Studies on the Total Synthesis of Lactacysin. An Improved Aldol Coupling reaction and a β-Lactona intermediates in Thiol Ester Formation, Tetrahedron Lett., 1993, vol. 34, No. 44, 6977-6980.
Corey, E. J.; Reichard, G. A., Total Synthesis of Lactacystin, J. Am. Chem. Soc., 1992, 114, 10677-10678.
Fenteany, G.; Standaert, R.F.; Reichard, G. A.; Corey, E. J.; Schreiber, S. L., A β-lactone related to lactacystin induces neurite outgrowth in a neuroblastoma cell line and inhibits cell cycle progression in an osteosarcoma cell line. Proc. Natl. Acad. Sci. USA, 1994, 91, 3358-3362.

Omura, S., Fujimoto, T., Otoguro, K., Matsuzaki, K. Moriguchi, R., Tanaka, H., Sasaki, Y., Lactacystin, A novel Microbial Metabolite, induces Neuritogenesis of Neuroblastoma Cells, A, J. Antibiot., 1991, 44, 113-116.
Omura, S., Matsuzaki, K. Fujimoto, T., Kosuga, K., Furuya, T., Fujita, S., Nakagawa, Structure of Lactacystin, a new microbial metabolite which induces differentiation of Neuroblastoma Cells. A., J. Antibiot., 1991, 44, 117-118.
Mincer, Tracy, J., Jensen, Paul, R., Kauffman, Christopher, A., and Fenical William, Widespread and Persistent Populations of a Major new Marine Actinomycete Taxon in Ocean Sediments, Appl. Environ. Microbiol., 68, 5005 (2002).
Wilson, Elizabeth, K., Plumbing the Ocean Depths for Drugs, Chemical & Engineering News, vol. 81, No. 3, pp. 37-38 (2003).
Frank, S. A.; Mergott, D. J., Roush, W. R., The Vinylogous Intramolecular Morita—Baylis—Hillman Reaction: Synthesis of Functianalized Cyclopentenes and Cyclohexenes with Trialkylphosphines as Nucleophilic Catalysts, J. Am. Chem. Soc., 2002, 124, 2404-2405.
Mergott, D.J., Frank, S. A., Roush, W. R., Application of the Intramolecular Vinylogous Morita-Baylis-Hillman Reaction toward the Synthesis of the Spinosyn A Tricyclic Nucleus. Org. Lett., 2002, vol. 4, No. 18, 3157-3160.

(Continued)

Primary Examiner—Joseph K. McKane
Assistant Examiner—Robert Shiao

(57) ABSTRACT

A simple and effective stereocontrolled synthesis of salinosporamide A(1)

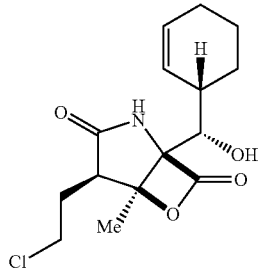

has been developed which follows the pathway outlined in the FIGURE. The process, the first total synthesis of salinosporamide A, is capable of providing the compound in substantial quantities for further biological studies. In addition to the method of Scheme I, the present invention also includes several novel synthetic intermediate compounds, several intermediate steps of the preferred synthetic process; and the uses of these compounds in the preparation of synthetic derivatives of the compound Salinosporamide A. Salinosporamide A is of special interest as a synthetic target because of its protein in vitro cytotoxic activity against many tumor cell lines ($IC_{50}$ values of 10 nM or less).

13 Claims, 1 Drawing Sheet

OTHER PUBLICATIONS

Aggarwal, V. K., Emme, I., Fulford, S. Y., Correlation between $pK_a$ and Reactivity of Quinuclidine-Based Catalysts in the Baylis-Hillman Reaction: Discovery of Quinuclidine as Optimum Catalyst Leading to Substantial Enhancement of Scope, J. Org. Chem., 2003, 68, 692-700.

Yeo J. E., Yang, X., Kim, H.J., Koo, S., The intramolecular Baylis-Hillman reaction: easy preparation of versatile substrates, facile reactions, and synthetic applications, J. Chem. Soc., Chem. Commun., 2004, 236-237.

Bols, M., Skrydstrup, T., Silicon-Tethered Reactions, Chem. Rev., 1995, 95, 1253-1277.

Fleming, I., Barbero, A., Walter, D., Sterechemical Control in Organic Synthesis Using Silicon-Containing Compounds, Chem. Rev., 1997, 97, 2063-2092.

Stork, G., Mook, R., Biller, S.A., Rychnovsky, S. D., Free-Radical Cyclization of Bromoacetals. Use in the Construction of Bicyclic Acetals and Lactones. J. Am. Chem. Soc., 1983, 105, 3741-3742.

Stork, G., Sher, P. M., Chen, H.L., Radical Cyclization-Trapping in the Synthesis of Natural Products. A Simple, Stereocontrolled Route to Prostaglandin $F_{2a}$. J. Am. Chem. Soc., 1986, 108, 6384-6385.

Miyake, H., Yamamura, K., Pd(0) Catlyzed Hydrostannation of Conjugated Dienes. A Facile and Highly Regio- and Stereoselective Synthesis of (Z)-2-Alkenylstannanes. Chem. Lett., 1992, 507-508.

Jones, G. R., Landais, Y., The Oxidation of the Carbon-Silicon Bond, Tetrahedron, 1996, 52, 7599-7662.

Corey, E. J., Li, W., Nagamitsu, T., An Efficient and Concise Enantioselective Total Synthesis of lactacystin. Angew. Chem. Int, Ed., 1998, 37, 1676-1679.

Corey, E.J., and Wei-Dong, Z., Total Synthesis and Biological Activity of Lactacystin, Omuralide and Analogs, Chem. Pharm Bull., 1999, 47, 1-10.

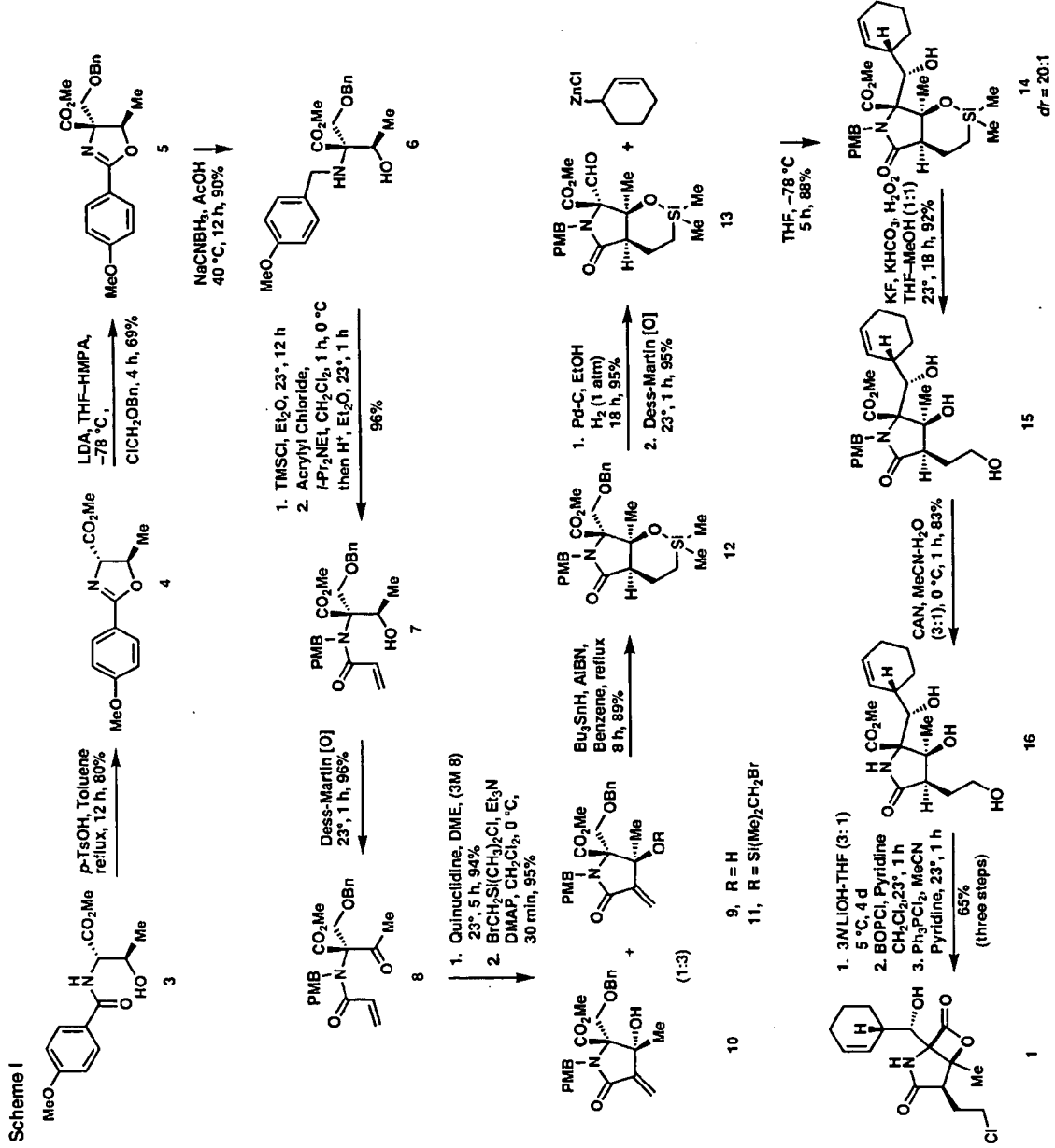

SIMPLE STEREOCONTROLLED SYNTHESIS OF SALINOSPORAMIDE A

BACKGROUND OF THE INVENTION

Salinosporamide A(1) was recently discovered by Fenical et al. as a bioactive product of a marine microorganism that is widely distributed in ocean sediments. Feeling, R. H.; Buchanan, G. O.; Mincer, T. J.; Kauffman, C. A.; Jensen, P. R.; Fenical, W., *Angew. Chem. Int. Ed.*, 2003, 42, 355–357.

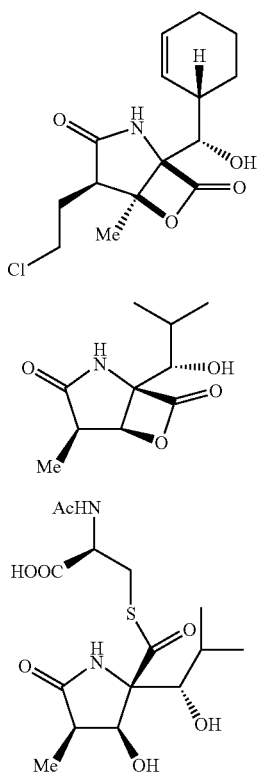

Structurally Salinosporamide A closely resembles the terrestrial microbial product omuralide (2a) that was synthesized by Corey et al. several years ago and demonstrated to be a potent inhibitor of proteasome function. See, (a) Corey, E. J.; Li, W. D., *Z. Chem. Pharm. Bull.*, 1999, 47, 1–10; (b) Corey, E. J., Reichard, G. A.; Kania, R., *Tetrahedron Lett.*, 1993, 34, 6977–6980; (c) Corey, E. J.; Reichard, G. A., *J. Am. Chem. Soc.*, 1992, 114, 10677–10678; (d) Fenteany, G.; Standaert, R. F.; Reichard, G. A.; Corey, E. J.; Schreiber, S. L., *Proc. Natl. Acad. Sci. USA*, 1994, 91, 3358–3362.

Omuralide is generated by β-lactonization of the N-acetylcysteine thiolester lactacystin (2b) that was first isolated by the Omura group as a result of microbial screening for nerve growth factor-like activity. See, Omura, S., Fujimoto, T., Otoguro, K., Matsuzaki, K., Moriguchi, R., Tanaka, H., Sasaki, Y., *Antibiot.*, 1991, 44, 113–116; Omura, S., Matsuzaki, K., Fujimoto, T., Kosuge, K., Furuya, T., Fujita, S., Nakagawa, A., *J. Antibiot.*, 1991, 44, 117–118.

Salinosporamide A, the first compound Fenical's group isolated from *Salinospora*, not only had a never-before-seen chemical structure 1, but is also a highly selective and potent inhibitor of cancer-cell growth. The compound is an even more effective proteasome inhibitor than omuralide and, in addition, it displays surprisingly high in vitro cytotoxic activity against many tumor cell lines ($IC_{50}$ values of 10 nM or less). Fenical et al. first found the microbe, which they've dubbed *Salinospora*, off the coasts of the Bahamas and in the Red Sea. See, *Appl. Environ. Microbiol.*, 68, 5005 (2002).

Fenical et al. have shown that *Salinospora* species requires a salt environment to live. *Salinospora* thrives in hostile ocean-bottom conditions: no light, low temperature, and high pressure. The Fenical group has now identified *Salinospora* in five oceans, and with 10,000 organisms per $cm^3$ of sediment and several distinct strains in each sample; and according to press reports, they've been able to isolate 5,000 strains. See, *Chemical & Engineering News*, 81, 37 (2003).

A great percentage of the cultures Fenical et al. have tested are said to have shown both anticancer and antibiotic activity. Like omuralide 2a, salinosporamide A inhibits the proteasome, an intracellular enzyme complex that destroys proteins the cell no longer needs. Without the proteasome, proteins would build up and clog cellular machinery. Fast-growing cancer cells make especially heavy use of the proteasome, so thwarting its action is a compelling drug strategy. See, Fenical et al., U.S. Patent Publication No. 2003-0157695A1, the disclosure of which is hereby incorporated herein by reference.

SUMMARY OF THE INVENTION

The present invention is directed to a method for the enantiospecific total synthesis of the compound of structure 1.

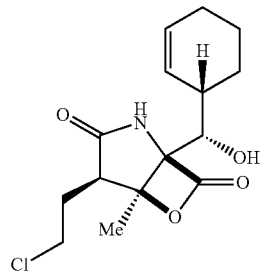

The preferred synthetic route to compound 1 is illustrated in the FIGURE accompanying this specification, and as discussed in greater detail below. In summary, the method of the present invention includes the following steps, which are detailed here with the preferred reagents and reaction conditions. The skilled artisan may likely be able to make substitutions of reagents and/or reaction conditions in any one or more of these reaction steps without necessarily departing from scope and teachings of the present invention:

(S)-Threonine methyl ester was N-acylated with 4-methoxybenzoyl chloride in $CH_2Cl_2$ at 23° C. to form the amide 3 (71%) which was then cyclized to oxazoline 4 (80%) by heating at reflux in toluene with p-toluenesulfonic acid.

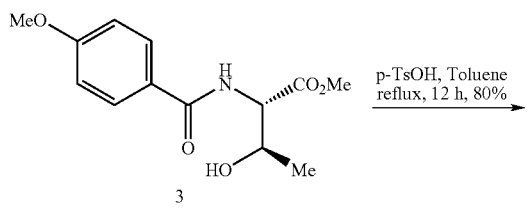

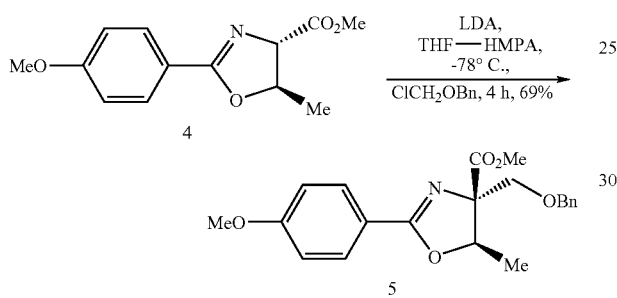

Deprotonation of 4 with lithium diisopropylamide in THF and alkylation of the resulting enolate with chloromethyl benzyl ether afforded the required tertiary stereocenter of 5 selectively in 69% yield.

Reduction of 5 with NaBH$_3$CN—HOAc gave the N-4-methoxybenzylamine 6 (90%).

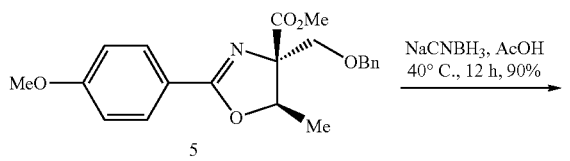

Compound 6 was then transformed in 96% yield to the N-acrylyl-N-PMB derivative 7 (PMB=4-methoxybenzyl) by the one flask, seqeuence: (1) reaction with Me$_3$SiCl and Et$_3$N to form the TMS ether (6a—OH is OTMS), followed by (2) acylation with acrylyl chloride at 0° C. and (3) acidic work up with aqueous HCl.

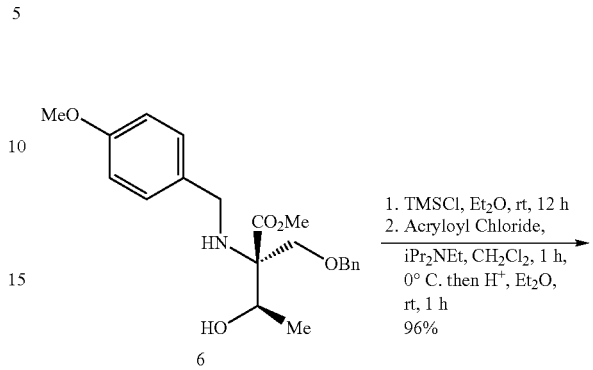

Dess-Martin periodinane oxidation of 7 produced the keto amide ester 8 in 96% yield.

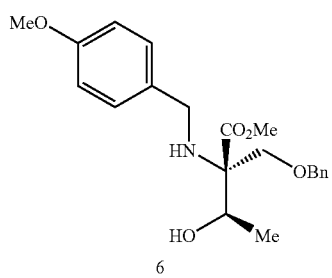

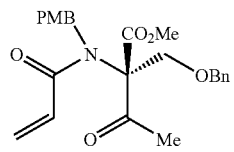

Cyclization of 8 to the γ-lactam 9 was accomplished by means of an internal Baylis-Hillman-aldol reaction using quinuclidine as the catalytic base in dimethoxyethane at 23° C. for 5 h. See, Frank, S. A.; Mergott, D. J., Roush, W. R., *J. Am. Chem. Soc.*, 2002, 124, 2404–2405. Mergott, D. J., Frank, S. A., Roush, W. R., *Org. Lett.*, 2002, 4, 3157–3160. Aggarwal, V. K., Emme, I., Fulford, S. Y., *J. Org. Chem.*, 2003, 68, 692–700. Yeo, J. E., Yang, X., Kim, H. J., Koo, S., *J. Chem. Soc., Chem. Commun.*, 2004, 236–237. The cyclization product, obtained in 94% yield consisted of 9 and the C(β) diastereomer (10) in a ratio of 3:1.

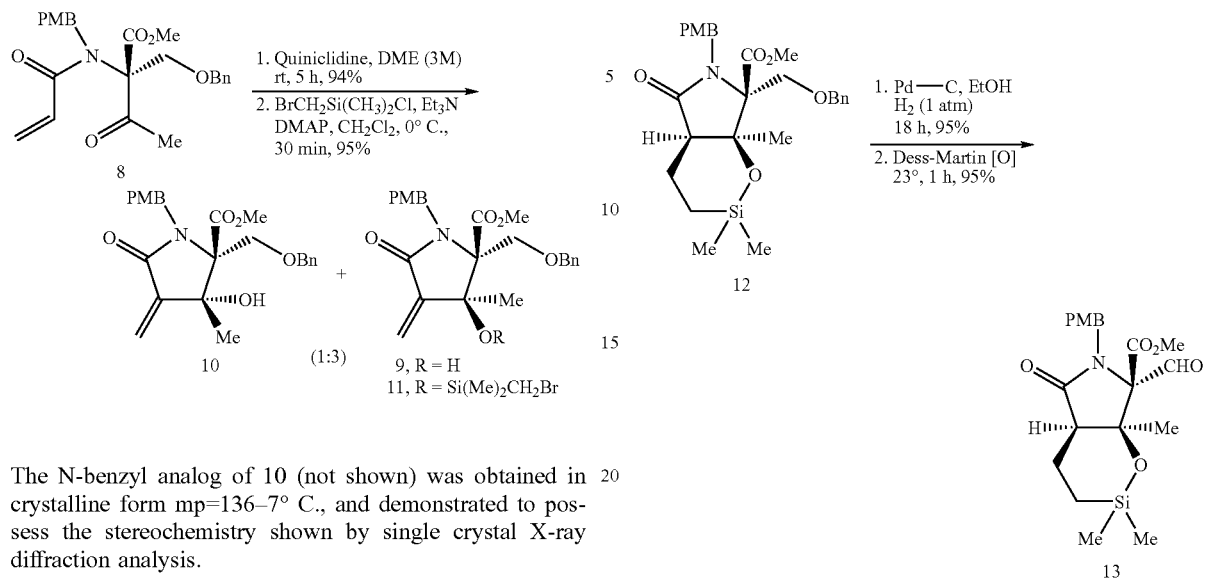

The N-benzyl analog of 10 (not shown) was obtained in crystalline form mp=136–7° C., and demonstrated to possess the stereochemistry shown by single crystal X-ray diffraction analysis.

Silylation of 9 with bromomethyldimethylsilyl chloride afforded 11 in 95% yield. Silyl ether 11 and the diastereomeric silyl ether were easily and conveniently separated at this stage by silica gel column chromatography on a preparative scale.

The required stereochemical relationship about C($\alpha$) and C($\beta$) of the $\gamma$-lactam core was established by tri-n-butyltin hydride-mediated radical-chain cyclization which transformed 11 cleanly into the cis-fused $\gamma$-lactam 12.

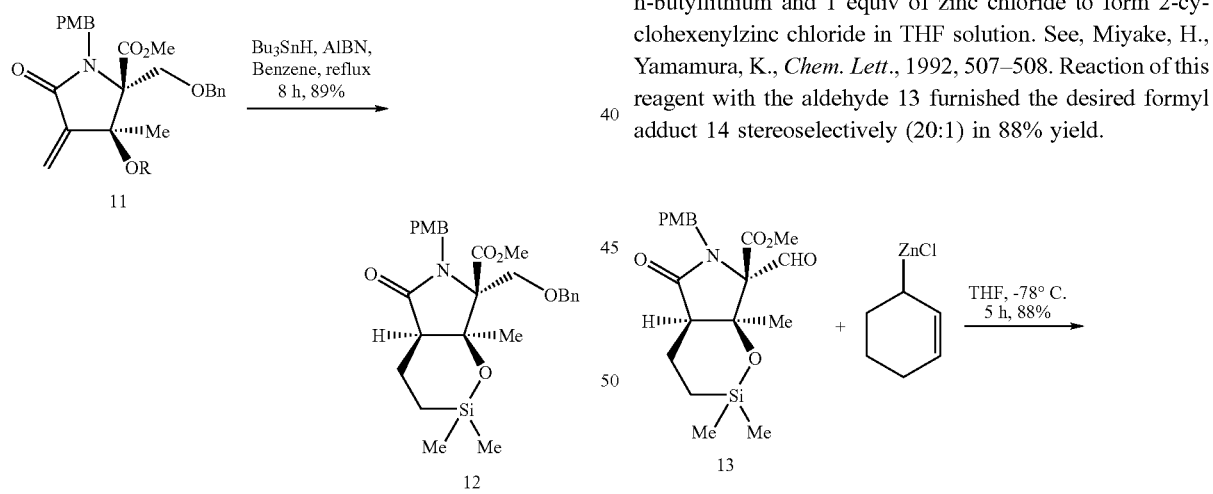

See, (a) Bols, M., Skrydstrup, T., *Chem. Rev.*, 1995, 95, 1253–1277. (b) Fleming, I., Barbero, A., Walter, D., *Chem. Rev.*, 1997, 97, 2063–2092. (c) Stork, G., Mook, R., Biller, S. A., Rychnovsky, S. D., *J. Am. Chem. Soc.*, 1983, 105, 3741–3742. (d) Stork, G., Sher, P. M., Chen, H. L., *J. Am. Chem. Soc.*, 1986, 108, 6384–6385.

Cleavage of the benzyl ether of 12 ($H_2$, Pd—C) afforded the primary alcohol (12a—OBn is OH), and Dess-Martin periodinane oxidation of 12a provided the aldehyde 13 in about 90% yield from 12.

The next step, the attachment of the 2-cyclohexenly group to the formyl carbon and the establishment of the remaining two stereocenters was accomplished in a remarkably simple way.

2-Cyclohexenyl-tri-n-butyltin (from Pd(O)-catalyzed 1,4-addition of tributyltin hybride to 1,3-cyclohexadiene) was sequentially transmetalated by treatment with 1 equiv of n-butyllithium and 1 equiv of zinc chloride to form 2-cyclohexenylzinc chloride in THF solution. See, Miyake, H., Yamamura, K., *Chem. Lett.*, 1992, 507–508. Reaction of this reagent with the aldehyde 13 furnished the desired formyl adduct 14 stereoselectively (20:1) in 88% yield.

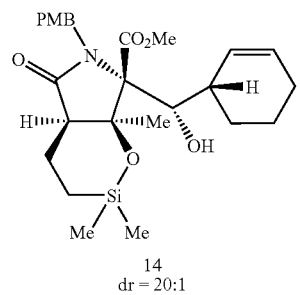

Tamao-Fleming oxidation of 14 gave the triol 15 in 92% yield.

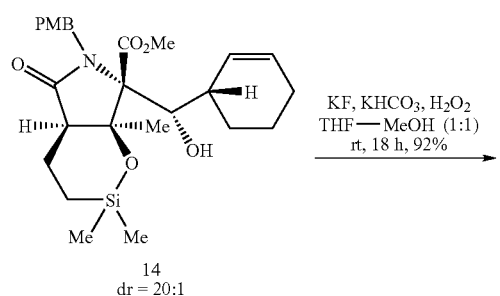

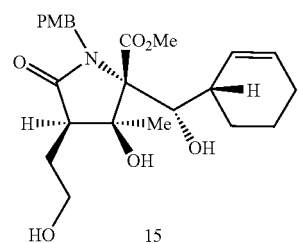

See, Fleming, T., *Chemtracts-Org. Chem.*, 1996, 9, 1–64, and Jones, G. R., Landais, Y., *Tetrahedron*, 1996, 52, 7599–7662.

Ce(IV)-induced oxidative cleavage of the PMB group of 15 afforded the triol ester 16:

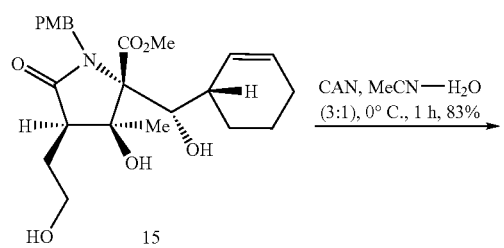

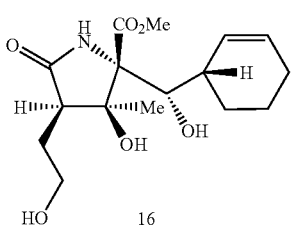

Compound 16 was then hydrolyzed to the corresponding γ-lactam-carboxylic acid 16a ($CO_2Me$ is $CO_2H$) using 3:1 aqueous 3N-lithium hydroxide and THF at 4° C.

The acid 16a was first cyclized to the beta-lactone 16b (1 where $CH_2CH_2Cl$ is $CH_2CH_2OH$), which is then converted to salinosporamide A(1) by successive reaction with 1.1 equiv of bis (2-oxo-3-oxazolidinyl) phosphinic chloride (BOPCl) and pyridine at 23° C. for 1 h, in 65% overall yield.

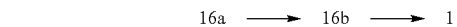

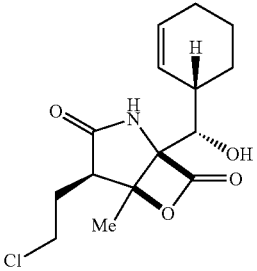

The identity of synthetic 1 and natural Salinosporamide A was established by comparison measurements of $^1H$ and $^{13}C$ NMR spectra, mp and mixed mp (168–170° C.), optical rotation, FTIR and mass spectra and chromatographic mobilities in three different solvent systems. Dr. Fenical graciously provided a sample of the natural product for this comparison.

There are a number of steps in the synthesis of 1 that require comment. The direct conversion of 6 to 7 with acrylyl chloride under a wide variety of conditions gave considerably lower yields than the process shown in Scheme 1 mainly because of competing O-acylation and subsequent further transformations.

The critical cyclization of 8 to 10 is still under investigation to find the conditions for maximizing the formation of 9 over the diastereomer 10. So far, quinuclidine has proved superior to other catalytic bases tried, e.g., 1,4-diaza[2.2.2] bicyclooctate. As indicated above, the attachment of the 2-cyclohexenyl group to aldehyde 13 to form 14 worked best with the reagent cyclohexenylzinc chloride.

The stereochemistry of the conversion 13 to 14, established by the identity of totally synthetic 1 with naturally formed salinosporamide A, is that predicted from a cyclic, chair-formed, six-membered transition state involving addition of the organozinc reagent to the sterically more accessible face of the formyl group. The use of 2-cyclo-hexenylzinc chloride may be critical to successful formation of 14 since none of this product is obtained with 2-cyclohexenyl-lithium (probably because the initial carbonyl adduct undergoes retroaldol cleavage and decomposition; see Corey, E. J., Li, W., Nagamitsu, T., *Angew. Chem. Int, Ed.*, 1998, 37, 1676–1679).

Attempts to form 14 from 13 using Lewis acid-catalyzed reaction with tri-n-butyl-2-cyclohexenyltin have thus far been unsuccessful. The saponification of methyl ester 16 at temperatures above +5° C. led to lowered yields of the required carboxylic acid. Finally, the one flask β-lactonization and chlorination reactions leading to 1 were remarkably clean and probably proceed in greater than 90% yield per step.

In addition to the method of Scheme I, preferred embodiments of the invention also include novel synthetic intermediate compounds, intermediate steps of the preferred synthetic process; and the uses of this method and/or intermediate compounds thereof, in the preparation of synthetic analogs or derivatives of the compound Salinosporamide A. Typical substituent modifications for compounds of this type are known to persons having ordinary skill in this art. See, for example, the substituent groups defined for analogs of lactacystin compounds as taught in Corey et al., *Chem. Pharm. Bull.*, 1999, 47, 1–10, the disclosure of which is incorporated herein by reference. Other substituent modifications will be apparent based upon the disclosures in related patents. See, for example, U.S. Pat. Nos. 6,645,999; 6,566,553; 6,458,825; 6,335,358; 6,294,560; 6,214,862; 6,147,223; 6,133,308; 5,869,675; 5,756,764; and PCT Publication No. WO 96/32105; the disclosures of which are hereby incorporated herein by reference.

BRIEF DESCRIPTION OF THE DRAWING

The FIGURE illustrates Scheme I, a preferred synthetic route used to achieve the enantiospecific total synthesis of the compound of structure 1.

DETAILED DESCRIPTION OF THE PREFERRED EMBODIMENT

As set forth above, one embodiment of the present invention comprises a simple and effective stereocontrolled synthesis of Salinosporamide A, the compound of formula (1). Scheme 1, shown in the FIGURE, is a preferred pathway to accomplish this synthesis, the details of which are provided in the following Examples.

Experimental Details

Part I. Synthesis of the Salinosporamide A

Part 2. Synthesis of the Cyclohexenyl Zinc Chloride

General.

All moisture sensitive reactions were performed under nitrogen gas in glassware that was flame-dried and equipped with a magnetic stir bar. Tetrahydrofuran (THF) and 1,2-dimethoxyethane (DME) were freshly distilled from sodium benzophenone ketyl before use. Hexanes, pyridine, triethylamine, pentane and dichloromethane were freshly distilled from $CaH_2$ before use. Toluene was distilled from sodium.

Thin-layer chromatography (TLC) was performed using E. Merck silica gel 60 $F_{254}$ pre-coated plates (0.25 mm). Flash chromatography was performed using Baker silica gel (40 µm particle size). All products were purified to homogeneity by TLC analysis (single spot/two solvent systems) using a UV lamp or CAM or PMA or anisaldehyde or basic $KMnO_4$ for detection purposes.

NMR spectra were recorded on 400 MHz, 500 MHz and 600 MHz spectrometers. $^1H$ and $^{13}C$ NMR chemical shifts are reported as δ using residual solvent as an internal standard. High-resolution mass spectral analyses were performed at Harvard University Mass Spectrometry Center.

Part I. Synthesis of the Salinosporamide A(1)

EXAMPLE 1

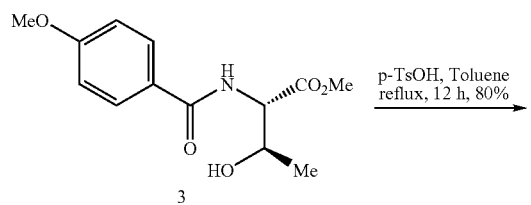

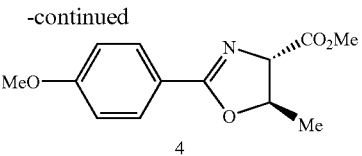

4

(4S, 5R) Methyl 4,5-dihydro-2 (4-methoxyphenyl)-5-methyloxazole-4-carboxylate (4)

A mixture of (2S, 3R)-methyl 2-(4-methoxybenzamido)-3-hydroxybutanoate (3) (35.0 g, 131 mmol) and p-TsOH.$H_2O$ (2.5 g, 13.1 mmol) in toluene (400 mL) was heated at reflux for 12 h. The reaction mixture was diluted with water (200 mL) and extracted with EtOAc (3×200 mL). The combined organic layers were washed with water, brine and dried over $Na_2SO_4$. The solvent was removed in vacuo to give crude oxazoline as yellow oil. Flash column chromatography on silica gel (eluent 15% EtOAc-Hexanes) afforded the pure oxazoline (26.1 g, 80%) as solid.

$R_f$=0.51 (50% ethyl acetate in hexanes), mp. 86–87° C.; $[\alpha]^{23}_D$+69.4 (c 2.0, $CHCl_3$); FTIR (film) $v_{max}$: 2955, 1750, 1545, 1355, 1187, 1011, 810 $cm^{-1}$; $^1HNMR(CDCl_3$, 400 MHz): δ 7.87 (2H, d, J=9.2 Hz), 6.84 (2H, d, J=8.8 Hz), 4.90 (1H, m), 4.40 (1H, d, J=7.6 Hz), 3.79 (3H,s), 3.71 (3H, s), 1.49 (3H, d, J=6.0 Hz); $^{13}C$ NMR ($CDCl_3$, 100 MHz): δ 171.93, 165.54, 162.64, 130.52, 119.80, 113.85, 78.91, 75.16, 55.51, 52.73, 21.14; HRMS (ESI) calcd for $C_{13}H_{16}NO_4$ (M+H)$^+$.250.1079, found 250.1084.

EXAMPLE 2

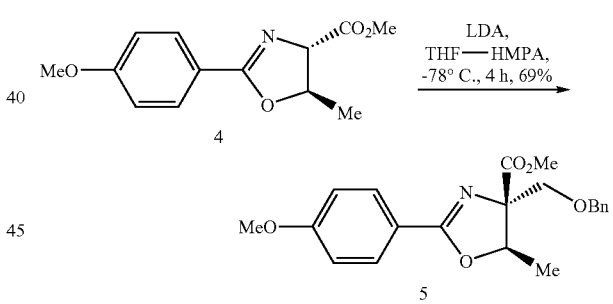

(4R, 5R)-Methyl 4-{(benzyloxy) methyl)}-4,5-dihydro-2-(4-methoxyphenyl)-5-methyloxazole-4-carboxylate (5)

To a solution of LDA (50 mmol, 1.0 M stock solution in THF) was added HMPA (24 mL, 215 mmol) at −78° C. and then oxazoline 4 (12.45 g, 50 mmol, in 20 mL THF) was added dropwise with stirring at −78° C. for 1 h to allow complete enolate formation. Benzyloxy chloromethyl ether (8.35 mL, 60 mmol) was added at this temperature and after stirring the mixture at −78° C. for 4 h, it was quenched with water (50 mL) and warmed to 23° C. for 30 min. Then the mixture was extracted with ethyl acetate (3×50 mL) and the combined organic phases were dried ($MgSO_4$) and concentrated in vacuo. The crude product was purified by column chromatography (silica gel, ethyl acetate/hexanes, 1:4 then 1:3) to give the benzyl ether 5 (12.7 g, 69%).

$R_f$=0.59 (50% ethyl acetate in hexanes). $[\alpha]^{23}_D$-6.3 (c 1.0, CHCl$_3$); FTIR (film) ($v_{max}$; 3050, 2975, 1724, 1642, 1607, 1252, 1027, 745, 697 cm$^{-1}$; $^1$H NMR (CDCl$_3$, 400 MHz): δ 7.96 (2H, d, J=9.2 Hz), 7.26 (5H, m), 6.90 (2H, J=8.8 Hz), 4.80 (1H, m), 4.61 (2H, s), 3.87 (3H, m), 3.81 (3H, s), 3.73 (3H, s), 1.34 (3H, d, J=6.8 Hz); $^{13}$C NMR (CDCl$_3$, 100 MHZ): 6171.23, 165.47, 162.63, 138.25, 130.64, 128.52, 127.87, 127.77, 120.15, 113.87, 81.40, 79.92, 73.91, 73.43, 55.58, 52.45, 16.92; HRMS (ESI) calcd for C$_{21}$H$_{24}$O$_5$ (M+H)$^+$370.1654, found 370.1644.

EXAMPLE 3

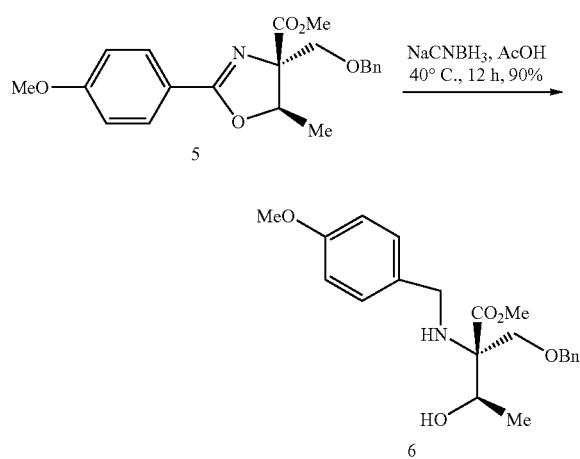

(2R,3R)-Methyl 2-(4-methoxybenzylamino)-2-((benzyloxy)methyl)-3hydroxybutanoate (6)

To a solution of oxazoline 5 (18.45 g, 50 mmol) in AcOH (25 mL) at 23° C. was added in portions NaCNBH$_3$ (9.3 g, 150 mmol). The reaction mixture was then stirred at 40° C. for 12 h to allow complete consumption of the starting material. The reaction mixture was diluted with water (100 mL), neutralized with solid Na$_2$CO$_3$ and the aqueous layer was extracted with ethyl acetate (3×100 mL). The combined organic phases were dried over NaSO$_4$ and concentrated in vacuo. The crude product was purified by column chromatography (silica gel, ethyl acetate/hexanes, 1:5) to give the N-PMB amino alcohol 6 (16.78 g, 90%).

$R_f$=0.50 (50% ethyl acetate in hexanes). $[\alpha]^{23}_D$-9.1(c 1.0, CHCl$_3$); FTIR (film) $v_{max}$; 3354, 2949, 1731, 1511, 1242, 1070, 1030, 820, 736, 697 cm$^{-1}$; $^1$H NMR (CDCl$_3$, 400 MHz): δ 7.32 (7H, m), 6.87 (2H, d, J=8.8 Hz), 4.55 (2H, m), 4.10 (1H, q, J=6.4 Hz), 3.85 (2H, dd, J=17.2, 10.0 Hz), 3.81 (3H, s,), 3.77 (3H, s), 3. 69 (2H, dd, J=22.8, 11.6 Hz), 3.22 (2H, bs), 1.16 (3H, d, J=6.0 Hz); $^{13}$C NMR (CDCl$_3$, 100 MHz): δ 173.34, 159.03, 137.92, 132.51, 129.78, 128.67, 128.07, 127.98, 114.07, 73.80, 70.55, 69.82, 69.65, 55.51, 55.29, 47.68, 18.15; HRMS (ESI) calcd. for C$_{21}$H$_{28}$NO$_5$ (M+H)$^+$ 374.1967, found 374.1974.

EXAMPLE 4

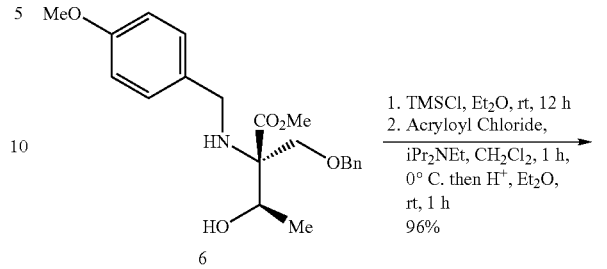

(2R,3R)-Methyl-2-(N-(4-methoxybenzyl)acrylamido)-2-(benzyloxy)methyl)-3-hydroxybutanoate (7)

A solution of amino alcohol 6 (26.2 g, 68.5 mmol) in Et$_2$O (200 mL) was treated with Et$_3$N (14.2 mL, 102.8 mmol) and trimethylchlorosilane (10.4 mL, 82.2 mmol) at 23° C. and stirred for 12 h. After completion, the reaction mixture was diluted with ether (200 mL) and then resulting suspension was filtered through celite. The solvent was removed to furnish the crude product (31.2 g, 99%) in quantitative yield as viscous oil. A solution of this crude trimethylsilyl ether (31.1 g) in CH$_2$Cl$_2$ (200 mL) was charged with diisopropylethylamine (14.2 mL, 81.6 mmol) and then cooled to 0° C. Acryloyl chloride (6.64 mL, 82.2 mmol) was added dropwise with vigorous stirring and the reaction temperature was maintained at 0° C. until completion (1 h). The reaction mixture was then diluted with CH$_2$Cl$_2$ (100 mL) and the organic layer was washed with water and brine. The organic layer was separated and dried over Na$_2$SO$_4$. The solvent was removed to afford the crude acrylamide 7 as a viscous oil. The crude product was then dissolved in Et$_2$O (200 mL) and stirred with 6N HCl (40 mL) at 23° C. for 1 h. The reaction mixture was diluted with water (100 mL) and concentrated to provide crude product. The residue was purified by column chromatography (silica gel, ethyl acetate/hexanes, 1:5 to 1:1) to give pure amide 7 (28.3 g, 96%) as colorless solid, mp 88–89° C.

$R_f$=0.40 (50% ethyl acetate in hexanes), $[\alpha]^{23}_D$-31.1 (c 0.45, CHCl$_3$), FTIR (film) $v_{max}$; 3435, 2990, 1725, 1649, 1610, 1512, 1415, 1287, 1242, 1175, 1087, 1029, 732, 698 cm$^{-1}$; $^1$H NMR (CDCl$_3$, 500 MHz): δ 7.25 (5H, m), 7.15 (2H, d, J=6.0 Hz), 6.85 (2H, d, J=7.5 Hz), 6.38 (2H, d, J=6.0 Hz), 5.55 (1H, t, J=6.0 Hz), 4.81 (2H, s), 4.71 (1H, q, J=6.5 Hz), 4.35 (2H, s), 4.00 (1H, d, J=10.0 Hz), 3.80 (1H, d, J=10.0 Hz), 3.76 (3H, s), 3.75 (3H, s), 3.28 (1H, bs), 1.22 (3H, d, J=6.0 Hz); $^{13}$C NMR (CDCl$_3$, 125 MHz): δ 171.87, 168.74, 158.81, 137.73, 131.04, 129.68, 128.58, 128.51, 127.94, 127.72, 127.20, 127.14, 114.21, 73.71, 70.42, 69.76, 67.65, 55.45, 52.52, 49.09, 18.88; HRMS (ESI) calcd. for C$_{24}$H$_{30}$NO$_6$ (M+H)$^+$428.2073, found 428.2073.

EXAMPLE 5

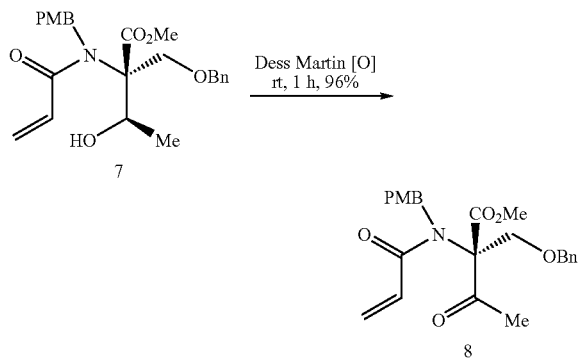

(R)-Methyl-2-(N-(4-methoxybenzyl)acrylamido)-2-(benzyloxy)methyl-3-oxybutanoate (8)

To a solution of amide 7 (10.67 g, 25.0 mmol) in CH$_2$Cl$_2$ (100 mL) was added Dess-Martin periodinane reagent (12.75 g, 30.0 mmol, Aldrich Co.) at 23° C. After stirring for 1 h, the reaction mixture was quenched with aq NaHCO$_3$—Na$_2$S$_2$O$_3$ (1:1, 50 mL) and extracted with ethyl acetate (3×50 mL). The organic phase was dried and concentrated in vacuo to afford the crude ketone. The crude product was purified by column chromatography (silica gel, ethyl acetate/hexanes) to give pure keto amide 8 (10.2 g, 96%).

R$_f$=0.80 (50% ethyl acetate in hexanes), mp 85 to 86° C.; [α]$^{23}_D$–12.8 (c 1.45, CHCl$_3$); FTIR (film) v$_{max}$: 3030, 2995, 1733, 1717, 1510, 1256, 1178, 1088, 1027, 733, 697 cm$^{-1}$; $^1$H NMR (CDCl$_3$, 500 MHz): δ 7.30 (2H, d, J=8.0), 7.25 (3H, m), 7.11 (2H, m), 6.88 (2H, d, J=9.0 Hz), 6.38 (2H, m), 5.63 (1H, dd, J=8.5, 3.5 Hz), 4.93 (1H, d, J=18.5 Hz), 4.78 (1H, d, J=18.5, Hz), 4.27 (2H, m), 3.78 (3H, s), 3.76 (3H, s), 2.42 (3H, s); $^{13}$C NMR (CDCl$_3$, 125 MHz): δ 198.12, 169.23, 168.62, 158.01, 136.95, 130.64, 130.38, 128.63, 128.13, 127.77, 127.32, 114.33, 77.49, 73.97, 70.66, 55.49, 53.09, 49.03, 28.24; HRMS (ESI) calcd. for C$_{24}$H$_{28}$NO$_6$ (M+H)$^+$ 426.1916, found 426.1909.

EXAMPLE 6

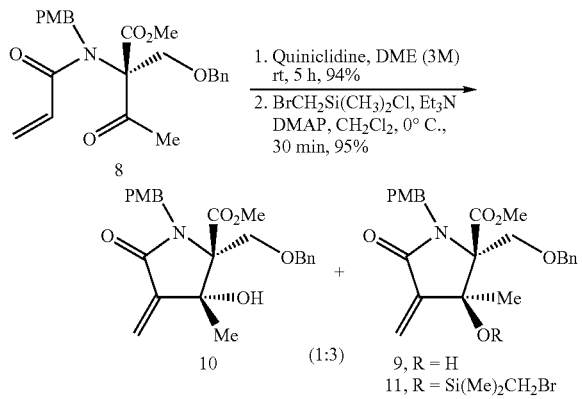

(2R,3S)-Methyl-1-(4-methoxybenzyl)-2-((benzyloxy)methyl)-3-hydroxy-3-methyl-4-methylene-5-oxopyrrolidine-2-carboxylate (9+10)

A mixture of keto amide 8 (8.5 g, 20.0 mmol) and quinuclidine (2.22 g, 20.0 mmol) in DME (10 mL) was stirred for 5 h at 23° C. After completion, the reaction mixture was diluted with ethyl acetate (50 mL) washed with 2N HCl, followed by water and dried over Na$_2$SO$_4$. The solvent was removed in vacuo to give the crude adduct (8.03 g, 94.5%, 3:1 ratio of 9 to 10 dr) as a viscous oil. The diastereomeric mixture was separated at the next step, although small amounts of 9 and 10 were purified by column chromatography (silica gel, ethyl acetate/hexanes, 1:10 to 1:2) for analytical purposes.

Major Diastereomer (9).

[α]$^{23}_D$–37.8 (c 0.51, CHCl$_3$); FTIR (film) v$_{max}$: 3450, 3055, 2990, 1733, 1683, 1507, 1107, 1028, 808,734 cm$^{-1}$; $^1$H NMR (CDCl$_3$, 500 MHz): δ 7.29 (5H, m), 7.15 (2H, d, J=7.5 Hz), 6.74 (2H, d, J=8.5 Hz), 6.13 (1H, s), 5.57 (1H, s), 4.81 (1H, d, J=14.5 Hz), 4.45(1H, d, J=15.0 Hz), 4.20 (1H, d, J=12.0 Hz), 4.10 (1H, d, J=12.0 Hz) 3.75 (3H, s), 3.70 (1H, d, J=10.5 Hz), 3.64 (3H, s), 3.54 (1H, d, J=10.5 Hz), 2.55 (1H, bs, OH), 1.50 (3H, s); $^{13}$C NMR (CDCl$_3$, 125 MHz): δ 169.67, 168.42, 158.97, 145.96, 137.57, 130.19, 130.12, 128.53, 127.83, 127.44, 116.79, 113.71, 76.32, 76.00, 73.16, 68.29, 55.45, 52.63, 45.36, 22.64; HRMS (ESI) calcd. for C$_{24}$H$_{28}$NO$_6$ (M+H)$^+$ 426.1916, found 426.1915.

Minor Diastereomer (10).

[α]$^{23}_D$–.50.1 (c 0.40, CHCl$_3$); FTIR (film) v$_{max}$: 3450, 3055, 2990, 1733, 1683, 1507, 1107, 1028, 808, 734 cm$^{-1}$; $^1$H NMR (CDCl$_3$, 500 MHz): δ 7.29 (5H, m), 7.12 (2H, d, J=7.5 Hz), 6.73 (2H, d, J=8.5 Hz), 6.12 (1H, s), 5.57 (1H, s), 4.88 (1H, d, J=15.5 Hz), 4.31 (1H, d, J=15.0 Hz), 4.08 (3H, m), 3.99 (1H, d, J=12.0 Hz) 3.73 (3H, s), 3.62 (3H, s), 3.47 (1H, bs, OH), 3.43 (1H, d, J=10.0 Hz), 1.31 (3H, s); $^{13}$C NMR (CDCl$_3$, 125 MHz): δ 169.65, 167.89, 159.13, 147.19, 136.95, 130.29, 129.76, 128.74, 128.19, 127.55, 116.80, 113.82, 76.21, 75.66, 73.27, 68.02, 55.45, 52.52, 45.24, 25.25; HRMS (ESI) calcd. for (M+H)$^+$ C$_{24}$H$_{28}$NO$_6$ 426.1916, found 426.1915.

EXAMPLE 7

Silylation of 9 and 10 and Purification of 11.

To a solution of lactams 9 and 10 (7.67 g, 18 mmol) in CH$_2$Cl$_2$ (25 ml) was added Et$_3$N (7.54 ml, 54 mmol), and DMAP (2.2 g, 18 mmol) at 0° C., and then bromomethyl-dimethylchlorosilane (5.05 g, 27 mmol) (added dropwise). After stirring the mixture for 30 min at 0° C., it was quenched with aq NaHCO$_3$ and the resulting mixture was extracted with ethyl acetate (3×50 mL). The combined organic layers were washed with water, brine and dried over Na$_2$SO$_4$. The solvent was removed in vacuo to give a mixture of the silated derivatives of 9 and 10 (9.83 g, 95%). The diastereomers were purified by column chromatography (silica gel, ethyl acetate/hexanes, 1:5 to 1:4) to give pure diastereomer 11 (7.4 g, 72%) and its diastereomer (2.4 g, 22%).

Silyl Ether (11).

R$_f$=0.80 (30% ethyl acetate in hexanes). [α]$^{23}_D$–58.9 (c 0.55, CHCl$_3$); FTIR (film) v$_{max}$: 3050, 2995, 1738, 1697, 1512, 1405, 1243, 1108, 1003, 809, 732 cm$^{-1}$; $^1$H NMR (CDCl$_3$, 500 MHz): δ 7.27 (5H, m), 7.05 (2H, d, J=7.0 Hz), 6.71 (2H, d, J=8.5 Hz), 6.18 (1H, s), 5.53 (1H, s), 4.95 (1H, d, J=15.5 Hz), 4.45 (1H, d, J=15.0 Hz), 4.02 (1H, J=12.0 Hz), 3.86 (1H, d, J=11.5 Hz) 3.72 (3H, s), 3.68 (3H, s), 3.65 (1H, d, J=10.5 Hz), 3.30 (1H, d, J=10.0 Hz), 2.34 (2H, d, J=2.0 Hz), 1.58 (3H, s), 0.19 (3H, s), 0.18 (3H, s); $^{13}$C NMR (CDCl$_3$, 125 MHz): δ 168.62, 168.12, 158.93, 145.24, 137.53, 130.32, 130.30, 128.49, 127.76, 127.22, 117.26, 113.60, 78.55, 78.03, 72.89, 68.45, 55.43, 52.37, 45.74, 21.87, 17.32, −0.72, −0.80; HRMS (ESI) Calcd. for C$_{27}$H$_{35}$BrNO$_6$Si (M+H)$^+$ 576.1417, found 576.1407.

EXAMPLE 8

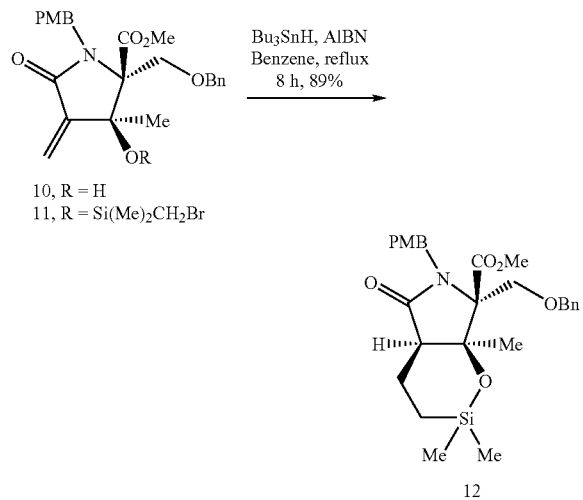

10, R = H
11, R = Si(Me)$_2$CH$_2$Br

12

Conversion of (11) to (12).

To a solution of compound 11 (5.67 g 10 mmol) in benzene (250 mL) at 80° C. under nitrogen was added a mixture of tributyltin hydride (4.03 ml, 15 mmol) and AIBN (164 mg, 1 mmol) in 50 ml benzene by syringe pump over 4 h. After the addition was complete, the reaction mixture was stirred for an additional 4 h at 80° C. and the solvent was removed in vacuo. The residue was dissolved in hexanes (20 mL) and washed with saturated NaHCO$_3$ (3×25 mL), water and dried over Na$_2$SO$_4$. The solvent was removed in vacuo to give crude product. The crude product was purified by column chromatography (silica gel, ethyl acetate/hexanes, 1:5) to afford the pure 12 (4.42 g, 89%).

R$_f$=0.80 (30% ethyl acetate in hexanes). [α]$^{23}_D$−38.8 (c 0.25, CHCl$_3$); FTIR (film) ν$_{max}$: 3025, 2985, 1756, 1692, 1513, 1247, 1177, 1059, 667 cm$^{-1}$; $^1$H NMR (CDCl$_3$, 500 MHz): δ 7.28 (5H, m), 7.09 (2H, d, J=7.0 Hz), 6.73 (2H, d, J=9.0 Hz), 4.96(1H, d, J=15.0 Hz), 4.35 (1H, d, J=15.5 Hz), 3.97 (1H, d, J=12.5 Hz), 3.86 (1H, d, J=12.0 Hz), 3.80 (1H, d, J=10.0 Hz), 3.72 (3H, s), 3.65 (3H, s), 3.27 (1H, d, J=10.5 Hz), 2.67 (1H, t, J=4.0 Hz), 2.41 (1H, m), 1.79 (1H, m), 1.46 (3H, s), 0.77 (1H, m), 0.46 (1H, m), 0.10 (3H, s), 0.19 (3H, s); $^{13}$C NMR (CDCl$_3$, 125 MHz): δ 175.48, 169.46, 158.76, 137.59, 131.04, 129.90, 128.58, 127.88, 127.52, 113.59, 113.60, 81.05, 78.88, 73.12, 69.03, 55.45, 51.94, 48.81, 45.50, 22.79, 17.06, 7.76, 0.54; HRMS (ESI) calcd. for (M+H)$^+$ C$_{27}$H$_{36}$NO$_6$Si 498.2312, found 498.2309.

EXAMPLE 9

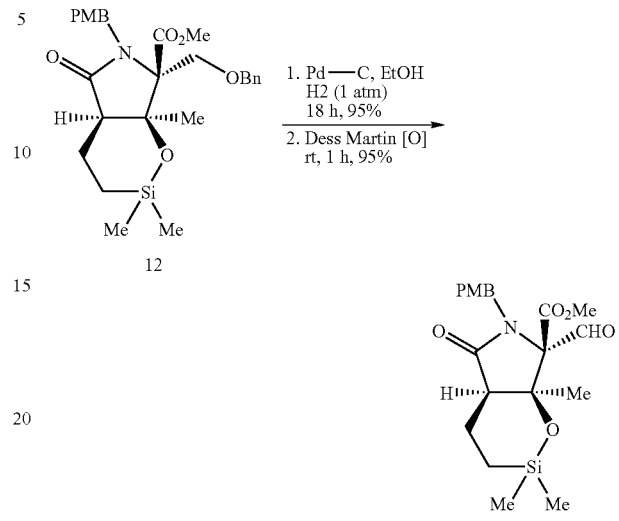

12

13

Debenzylation of (12).

A solution of 12 (3.98 g, 8 mmol) in EtOH (50 ml) at 23° C. was treated with 10% Pd—C (~1 g) under an argon atmosphere. The reaction mixture was evacuated and flushed with H$_2$ gas (four times) and then stirred vigorously under an atmosphere of H$_2$ (1 atm, H$_2$ balloon) at 23° C. After 12 h, the reaction mixture was filtered through Celite and concentrated in vacuo to give the crude debenzylation product (3.08 g, 95%) which was used for the next step. A small amount crude product was purified by column chromatography (silica gel, ethyl acetate/hexanes, 1:3) for analytical purposes. R$_f$=0.41 (50% ethyl acetate in hexanes).

mp, 45–47° C.; [α]$^{23}_D$−30.9 (c 0.55, CHCl$_3$); FTIR (film) ν$_{max}$: 3432, 3020, 2926, 1735, 1692, 1512, 1244, 1174, 1094, 1024, 870, 795 cm$^{-1}$; $^1$H NMR (CDCl$_3$, 400 MHz): δ 7.36 (2H, d, J=8.5 Hz), 6.83 (2H, d, J=8.5 Hz), 5.16 (1H, d, J=15.0 Hz), 4.29 (1H, d, J=15.0 Hz), 3.92 (1H, m), 3.78 (3H, s), 3.68 (3H, s), 3.45 (1H, m), 2.53 (1H, t, J=4.0 Hz), 2.42 (1H, m), 1.82 (1H, m), 1.50 (3H, s), 1.28 (1H, m), 0.75 (1H, m), 0.47 (1H, m), 0.11 (3H, s), 0.02 (3H, s); $^{13}$C NMR (CDCl$_3$, 125 MHz): δ 175.82, 169.51, 159.32, 131.00, 129.72, 114.52, 80.79, 80.13, 61.85, 55.48, 51.99, 49.29, 45.06, 23.11, 17.03, 7.44, 0.54; HRMS (ESI) calcd. for C$_{20}$H$_{30}$NO$_6$Si (M+H)$^+$ 408.1842, found 408.1846.

EXAMPLE 10

Oxidation to Form Aldehyde (13).

To a solution of the above alcohol from debenzylation of 12 (2.84 g, 7 mmol) in CH$_2$Cl$_2$ (30 mL) was added Dess-Martin reagent (3.57 g, 8.4 mmol) at 23° C. After stirring for 1 h at 23° C., the reaction mixture was quenched with aq NaHCO$_3$—Na$_2$S$_2$O$_3$ (1:1, 50 mL) and extracted with ethyl acetate (3×50 mL). The organic phase was dried and concentrated in vacuo to afford the crude aldehyde. The crude product was purified by column chromatography (silica gel, ethyl acetate/hexanes, 1:5) to give pure aldehyde 13 (2.68 g, 95%). R$_f$=0.56 (50% ethyl acetate in hexanes).

mp, 54–56° C.; [α]$^{23}_D$−16.5 (c 0.60, CHCl$_3$); FTIR (film) ν$_{max}$: 3015, 2925, 1702 1297, 1247, 1170, 1096, 987, 794 cm$^{-1}$; $^1$H NMR (CDCl$_3$, 500 MHz): δ 9.62 (1H, s), 7.07 (2H, d, J=8.0 Hz), 6.73 (2H, d, J=8.5 Hz), 4.49 (1H, quart, J=8.5 Hz), 3.70 (3H, s), 3.67 (3H, s), 2.36 (2H, m), 1.75 (1H, m), 1.37 (3H, s), 0.73 (1H, m), 0.48 (1H, m), 0.07 (3H, s), 0.004 (3H, s); $^{13}$C NMR (CDCl$_3$, 125 MHz): δ 197.26, 174.70, 167.36, 158.07, 130.49, 128.96, 113.81, 83.97, 82.36, 55.34, 52.43, 47.74, 46.32, 23.83, 16.90, 7.52, 0.56, 0.45; HRMS (ESD calcd. for C$_{20}$H$_{28}$NO$_6$Si (M+H)$^+$ 406.1686, found 406.1692.

EXAMPLE 11

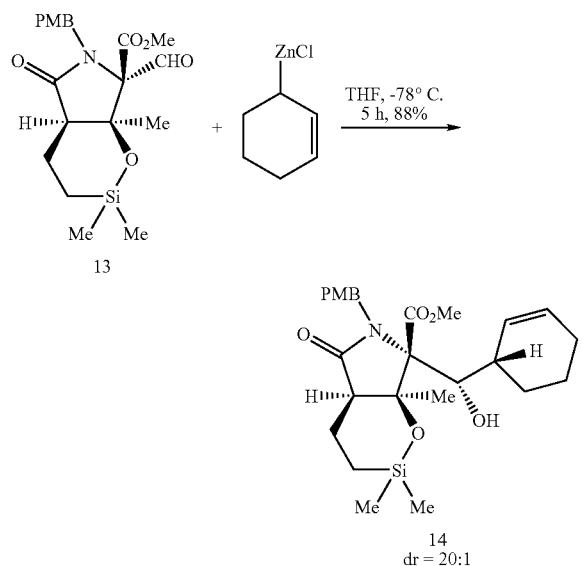

Conversion of (13) to (14).

To a solution of freshly prepared cyclohexenyl zinc chloride (10 mL, 0.5 M solution in THF, 5 mmol) (see Example 15 below) at −78° C. under nitrogen was added a −78° C. solution of aldehyde 13 (1.01 g, in 3 ml of THF, 2.5 mmol). After stirring for 5 h at −78° C. reaction mixture was quenched with water (10 mL) then extracted with ethyl acetate (3×10 mL). The combined organic layers were dried over Na$_2$SO$_4$ and solvent was removed in vacuo to give crude product (20:1 dr). The diastereomers were purified by column chromatography (silica gel, ethyl acetate/hexanes, 1:10 to 1:2 affords the pure major diastereomer 14 (1.0 g, 83%) and a minor diastereomer (50 mg 5%). For 14: R$_f$=0.56 (50% ethyl acetate in hexanes).

mp, 79–81° C.; [a]$^{23}$$_D$−28.5 (c 1.45, CHCl$_3$); FTIR (film) ν$_{max}$: 3267, 2927, 2894, 2829, 1742, 1667, 1509, 1248, 1164, 1024, 795 cm$^{-1}$; $^1$H NMR (CDCl$_3$, 500 MHz): δ 7.34 (2H, d, J=8.5 Hz), 6.81 (2H, d, J=9.0 Hz), 5.84 (1H, m), 5.73 (1H, m), 4.88 (1H, d, J=15.5 Hz), 4.39 (1H, d, J=14.5 Hz), 4.11 (1H, t, J=6.5 Hz), 3.77 (3H, s), 3.58 (3H, s), 3.00 (1H, m), 2.95 (1H, d, J=9.0 Hz), 2.83 (1H, t, J=3.5 Hz), 3.36 (1H, m), 2.27 (1H, m), 1.98 (2H, m), 1.74 (3H, m), 1.62 (3H, s), 1.14 (2H, m), 0.59 (1H, m), 0.39 (11H, m), 0.13 (3H, s), 0.03 (3H, s); $^{13}$C NMR (CDCl$_3$, 125 MHz): δ 176.80, 170.03, 158.27, 131.86, 131.34, 128.50, 126.15, 113.40, 83.96, 82.45, 77.17, 55.45, 51.46, 48.34, 48.29, 39.08, 28.34, 25.29, 22.45, 21.09, 17.30, 7.75, 0.39, 0.28; HRMS (ESI) calcd. for C$_{26}$H$_{38}$NO$_6$Si (M+H)$^+$ 488.2468, found 488.2477.

EXAMPLE 12

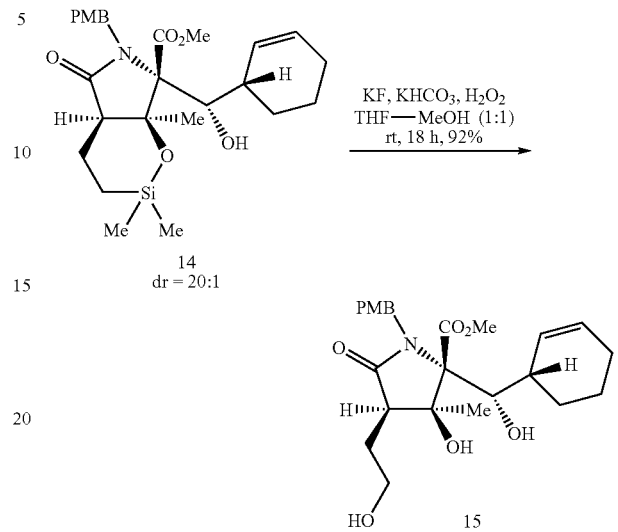

Tamao-Fleming Oxidation of (14) to (15).

To a solution of 14 (0.974 g, 2 mmol) in THF (5 mL) and MeOH (5 mL) at 23° C. was added KHCO$_3$ (0.8 g, 8 mmol) and KF (0.348 g, 6 mmol). Hydrogen peroxide (30% in water, 5 mL) was then introduced to this mixture. The reaction mixture was vigorously stirred at 23° C. and additional hydrogen peroxide (2 ml) was added after 12 h. After 18 h, the reaction mixture was quenched carefully with NaHSO$_3$ solution (15 mL). The mixture was extracted with ethyl acetate (3×25 mL) and the combined organic layers were washed with water and dried over Na$_2$SO$_4$. The solvent was removed in vacuo to give the crude product. The crude product was purified by column chromatography (silica gel, ethyl acetate) to give the pure triol 15 (0.82 g, 92%).

R$_f$=0.15 (in ethyl acetate). mp, 83–84° C.; [α]$^{23}$$_D$: +5.2 (c 0.60, CHCl$_3$); FTIR (film) ν$_{max}$; 3317, 2920, 2827, 1741, 1654, 1502, 1246, 1170, 1018, 802 cm$^{-1}$; $^1$HNMR(CDCl$_3$, 500 MHz): δ 7.77 (2H, d, J=8.0 Hz), 6.28 (2H, d, J=8.0 Hz), 5. 76 (1H, m), 5.63 (1H, d, J=10.0 Hz), 4.74 (1H, d, J=15.5 Hz), 4.54 (1H, d, J=15.0 Hz), 4.12 (1H, d, J=2.5 Hz), 3.80 (1H, m), 3.76 (3H, s), 3.72 (1H, m), 3.68 (3H, s), 3.00 (1H, m), 2.60 (1H, br), 2.20 (1H, m), 1.98 (2H, s), 1.87 (1H, m), 1.80 (1H, m), 1.71 (2H, m), 1.61 (3H, s), 1.14 (2H, m); $^{13}$C NMR (CDCl$_3$, 125 MHz): δ 178.99, 170.12, 158.27, 131.30, 130.55, 128.13, 126.39, 113.74, 81.93, 80.75, 76.87, 61.61, 55.45, 51.97, 51.32, 48.07, 39.17, 27.71, 27.13, 25.22, 21.35, 21.22; HRMS (ESI) calcd. for C$_{24}$H$_{34}$NO$_7$ (M+H)$^+$ 448.2335, found 448.2334.

EXAMPLE 13

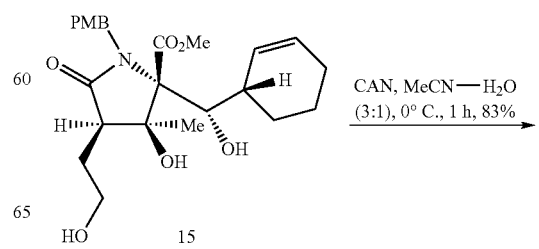

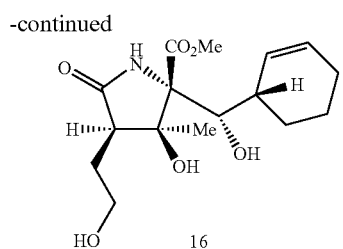

Deprotection of (15) to (16).

To a solution of 15 (0.670 g, 1.5 mmol) in acetonitrile (8 mL) at 0° C. was added a pre-cooled solution of ceric ammonium nitrate (CAN) (2.46 g 4.5 mmol in 2 mL $H_2O$). After stirring for 1 h at 0° C. the reaction mixture was diluted with ethyl acetate (50 mL), washed with saturated NaCl solution (5 mL) and organic layers was dried over $Na_2SO_4$. The solvent was removed in vacuo to give the crude product which was purified by column chromatography (silica gel, ethyl acetate) to give the pure 16 (0.4 g, 83%).

$R_f$=0.10 (5% MeOH in ethyl acetate). mp, 138 to 140° C.; $[\alpha]^{23}_D$+14.5 (c 1.05, $CHCl_3$); FTIR (film) $v_{max}$ 3301, 2949, 2911, 2850, 1723, 1673, 1437, 1371, 1239, 1156, 1008, 689 $cm^{-1}$; $^1$H NMR ($CDCl_3$, 600 MHz): δ 8.48 (1H, br), 6.08 (1H, m), 5.75 (1H, d, J=9.6 Hz), 5.29 (1H, br), 4.13 (1H, d, J=6.6 Hz), 3.83 (3H, m), 3.79 (1H, m), 3.72 (1H, m), 2.84 (1H, d, J=10.2 Hz), 2.20 (1H, m), 2.16 (1H, br), 1.98 (3H, m), 1.77 (3H, m), 1.59 (1H, m), 1.54 (3H, s), 1.25 (1H, m). $^{13}$C NMR ($CDCl_3$, 125 MHz): δ 180.84, 172.95, 135.27, 123.75, 82.00, 80.11, 75.56, 62.39, 53.14, 51.78, 38.95, 28.79, 26.48, 25.04, 20.66, 19.99; HRMS (ESI) calcd. $(M+H)^+$ for $C_{16}H_{26}NO_6$ 328.1760, found 328.1752.

EXAMPLE 14 was removed in vacuo and the residue was extracted with EtOAc, separated, and concentrated in vacuo to give the crude trihydroxy carboxylic acid 16a (not shown). The crude acid was suspended in dry $CH_2Cl_2$ (2 mL), treated with pyridine (0.5 mL) and stirred vigorously at 23° C. for 5 min. To this solution was added BOPCl (152 mg, 0.6 mmol) at 23° C. under argon, and stirring was continued for 1 h. The solvent was removed under high vacuum and the residue was suspended in dry $CH_3CN$ (1 mL) and treated with pyridine (1 mL). To this solution was added $PPh_3Cl_2$ (333 mg, 1.0 mmol) at 23° C. under argon with stirring. After 1 h the solvent was removed in vacuo. The crude product was purified by column chromatography (silica gel, ethyl acetate-$CH_2Cl_2$, 1:5) to give the pure β-lactone 1 (100 mg, 64%) as a colorless solid.

$R_f$=0.55 (50% ethyl acetate in hexane). mp, 168–170° C. (authentic sample: 168–170° C., 169–171° C. in *Angew. Chem. Int. Ed.*, 2003, 42, 355–357); mixture mp, 168–170C. $[\alpha]^{23}_D$ −73.2 (c 0.49, MeOH), −72.9 (c 0.55, MeOH, in *Angew. Chem. Int. Ed.*, 2003, 42, 355–357); FTIR (film) $v_{max}$: 3406, 2955, 2920, 2844, 1823, 1701, 1257, 1076, 1012, 785, 691 $cm^{-1}$; $^1$H NMR ($CDCl_3$, 500 MHz): δ 10.62 (1H, br), 6.42 (1H, d, J=10.5 Hz), 5.88 (1H, m), 4.25 (1H, d, J=9.0 Hz), 4.14 (1H, m), 4.01 (1H, m), 3.17 (1H, t, J=7.0 Hz), 2.85 (1H, m), 2.48 (1H, m), 2.32 (2H, m), 2.07 (3H, s), 1.91 (2H, m), 1.66 (2H, m), 1.38 (1H, m); $^{13}$C NMR ($CDCl_3$, 125 MHz): δ 176.92, 169.43, 129.08, 128.69, 86.32, 80.35, 70.98, 46.18, 43.28, 39.31, 29.01, 26.47, 25.35, 21.73, 20.00; HRMS (ESI) calcd. for $(M-H)^-$ $C_{15}H_{19}ClNO_4$ 312.1003, found 312.1003.

Part 2. Synthesis of the 2-Cyclohexenylzinc chloride

EXAMPLE 15

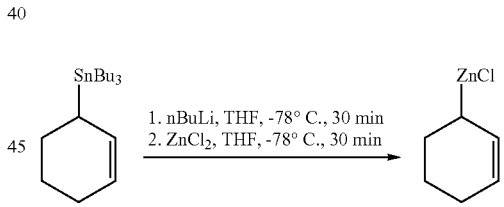

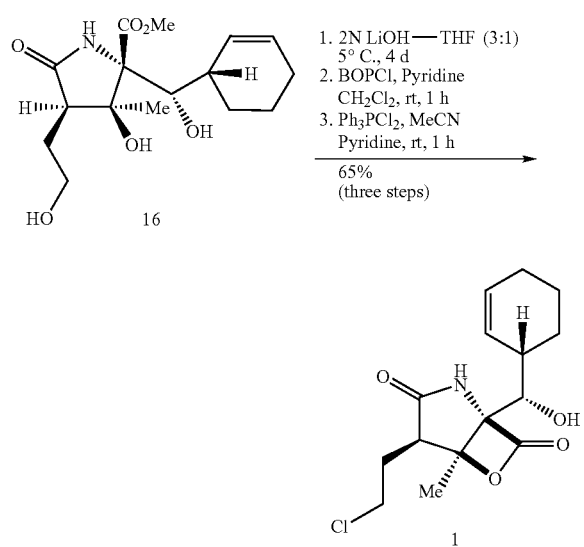

Conversion of (16) to Salinosporamide A(1).

A solution of triol ester 16 (0.164 g, 0.5 mmol) in 3 N aq LiOH (3 mL) and THF (1 mL) was stirred at 5° C. for 4 days until hydrolysis was complete. The acid reaction mixture was acidified with phosphoric acid (to pH 3.5). The solvent Synthesis of the Cyclohexenylzinc chloride.

To a solution of cyclohexenyltributyl tin (1.85 g 5 mmol) in THF (5 ml) at −78° C. under nitrogen was added nBuLi (2 ml, 2.5M solution in hexane, 5 mmol). See Miyake, H., Yamamura, K., *Chem. Lett.*, 1992, 507–508. After an additional 30 min stirring, $ZnCl_2$ (5 ml, 1 M solution in THF, 5 mmol) was added and stirring was continued at this temperature for 30 min at −78° C. to give a 0.5M solution of 2-cyclohexenylzinc chloride for reaction with the aldehyde 13 (see p S12).

The present invention has been described in detail, including the preferred embodiments thereof. However, it will be appreciated that those skilled in the art, upon consideration of the present disclosure, may make modifications and/or improvements on this invention and still be within the scope of this invention as set forth in the following claims.

What is claimed is:

1. A process for the enantiospecific total synthesis of the compound of structure 1:

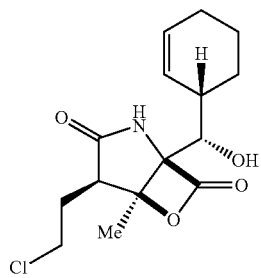
1 comprising the steps of:

(a) converting amide 3 to oxazoline 4:

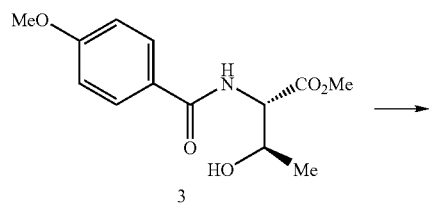

(b) deprotonating 4 followed by alkylation of the resulting enolate to provide 5:

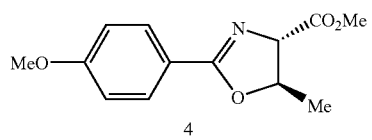

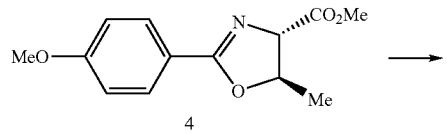

(c) reducing 5 to yield the N-4-methoxybenzylamine 6:

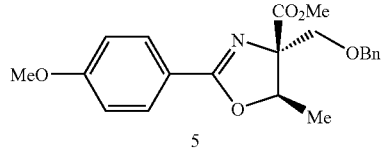

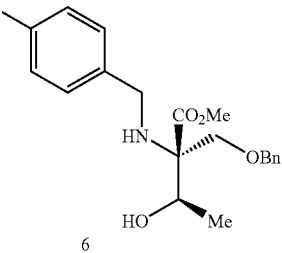
6

(d) acylating 6a (structure not shown, OH in 6 is OTMS) to afford the N-acrylyl-N-PMB derivative 7:

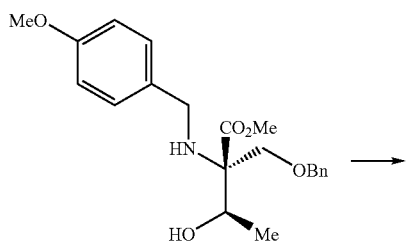

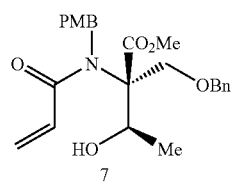
7

(e) oxidizing 7 to produce the keto amide ester 8:

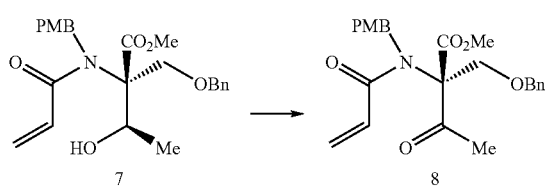

(f) cyclizing 8 to afford the γ-lactam 9:

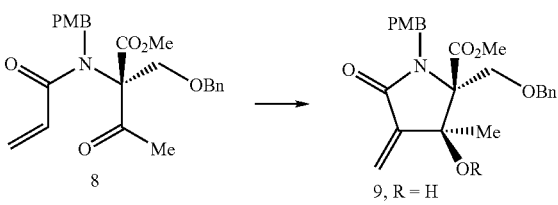

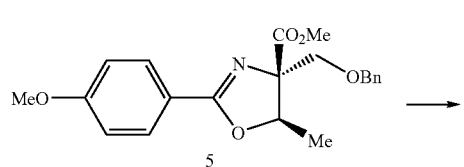

(g) silylating 9 to produce the silyl ether 11:

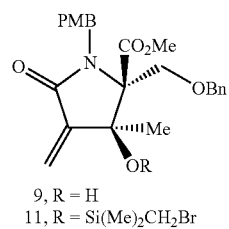

9, R = H
11, R = Si(Me)$_2$CH$_2$Br (h) cyclizing 11 to provide the cis-fused γ-lactam 12:

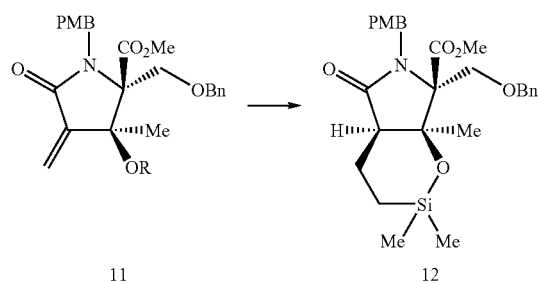

11    12

(i) cleaving the protecting group (OBn) in compound 12 to yield the primary alcohol 12a (wherein OBn in 12 is OH), and oxidizing 12a to provide the aldehyde 13:

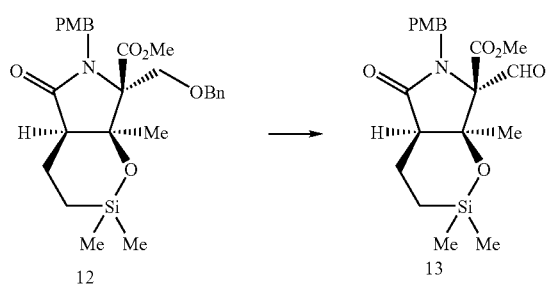

12    13

(j) reacting 2-cyclo-hexenyizine chloride with the aldehyde 13 to yield the formyl adduct 14:

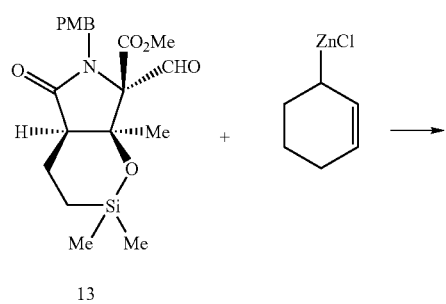

13

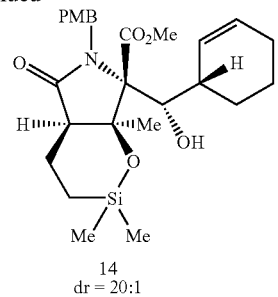

14
dr = 20:1

(k) oxidizing 14 to provide the triol 15:

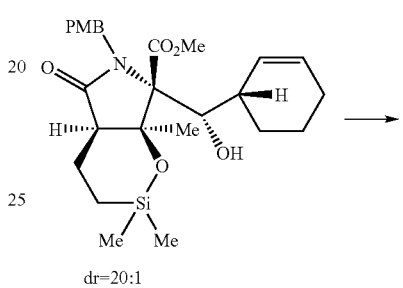

14
dr=20:1

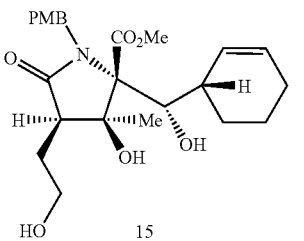

15

(l) cleaving the PMB group of 15 to yield the triol ester 16:

15

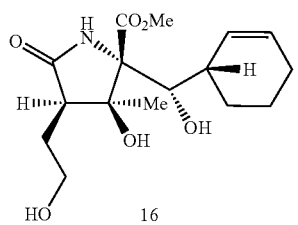

16

(m) hydrolyzing 16 to the corresponding γ-lactam-carboxylic acid 16a (CO$_2$Me in 16 is CO$_2$H), followed by conversion of the acid 16a to the beta-lactone 16b, followed by conversion to salinosporamide A(1):

16 → 16a → 16b →

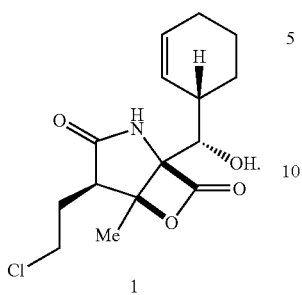

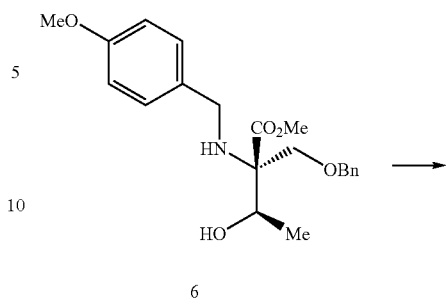

2. The intermediate step (b) of claim 1, namely the deprotonation of 4 followed by alkylation of the resulting enolate to provide 5:

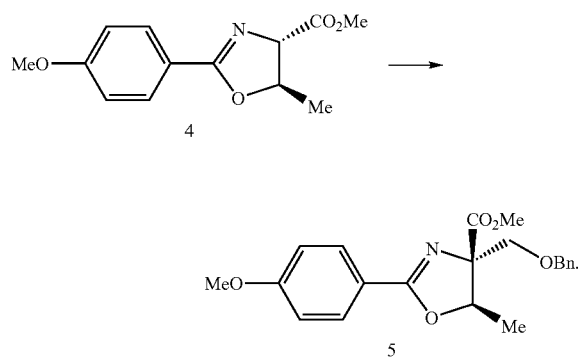

3. The intermediate step (c) of claim 1, namely the reduction of 5 to yield the N-4-methoxybenzylamine 6:

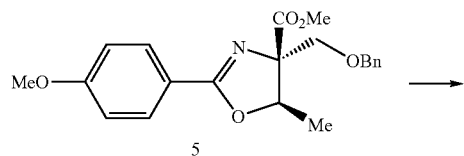

4. The intermediate step (d) of claim 1, namely the acylation of 6 to afford the N-acrylyl-N-PMB derivative 7:

5. The intermediate step (e) of claim 1, namely the oxidation of 7 to produce the keto amide ester 8:

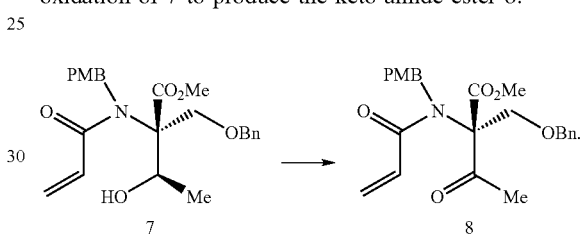

6. The intermediate step (f) of claim 1, namely the cyclization of 8 to afford the γ-lactam 9:

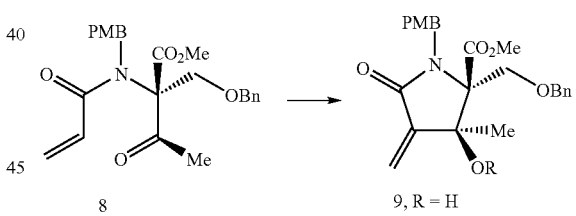

7. The intermediate step (g) of claim 1, namely the silylation of 9 to produce the silyl ether 11:

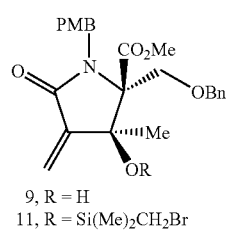

9, R = H
11, R = Si(Me)₂CH₂Br

8. The intermediate step (h) of claim 1, namely the cyclization of 11 to provide the cis-fused γ-lactam 12:

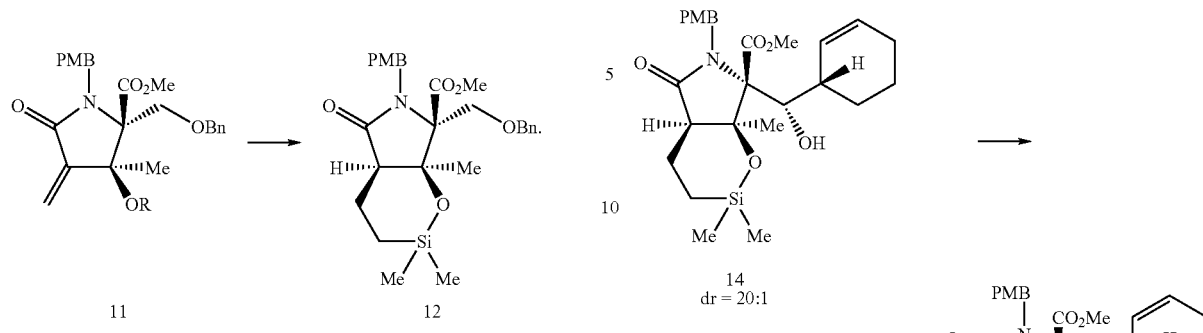

9. The intermediate step (i) of claim 1, namely the oxidation of 12 to provide the aldehyde 13:

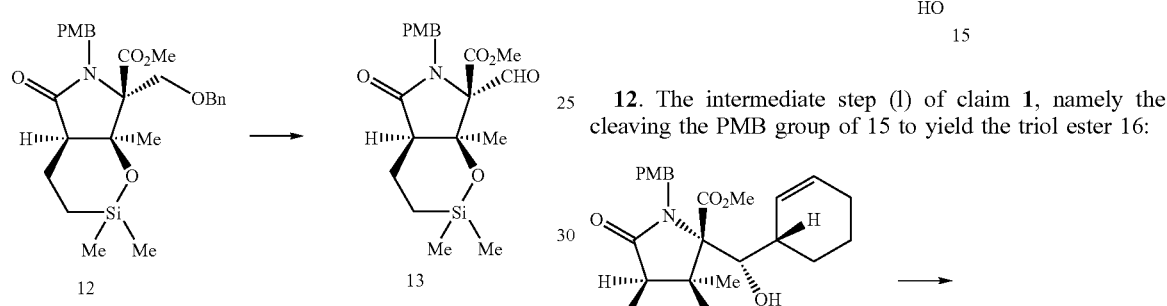

10. The intermediate step (j) of claim 1, namely the reaction of 2-cyclo-hexenyizine chloride with the aldehyde 13 to yield the formyl adduct 14:

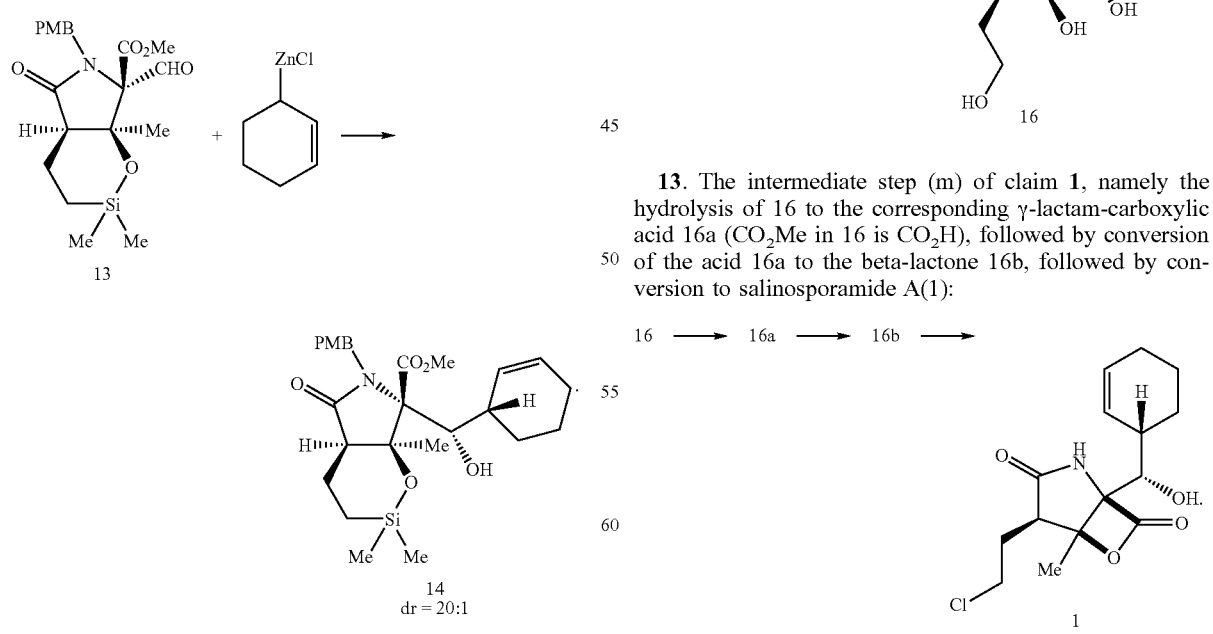

11. The intermediate step (k) of claim 1, namely the oxidation of 14 to provide the triol 15:

12. The intermediate step (l) of claim 1, namely the cleaving the PMB group of 15 to yield the triol ester 16:

13. The intermediate step (m) of claim 1, namely the hydrolysis of 16 to the corresponding γ-lactam-carboxylic acid 16a ($CO_2Me$ in 16 is $CO_2H$), followed by conversion of the acid 16a to the beta-lactone 16b, followed by conversion to salinosporamide A(1):

16 ⟶ 16a ⟶ 16b ⟶

* * * * *